United States Patent [19]

Heikkila

[11] Patent Number: 4,500,835
[45] Date of Patent: Feb. 19, 1985

[54] METHOD AND APPARATUS FOR DETECTING GRAIN DIRECTION IN WOOD, PARTICULARLY IN LUMBER

[75] Inventor: Sakari Heikkila, Espoo, Finland

[73] Assignee: A. Ahlstrom Osakeyhtio, Karhula, Finland

[21] Appl. No.: 383,588

[22] Filed: Jun. 1, 1982

Related U.S. Application Data

[63] Continuation-in-part of Ser. No. 042,517, May 25, 1979, abandoned.

[30] Foreign Application Priority Data

Jun. 1, 1978 [FI] Finland .................................. 781738

[51] Int. Cl.³ ........................................... G01R 27/04
[52] U.S. Cl. ............................................. 324/58.5 R
[58] Field of Search ..................... 324/58.5 A, 58.5 B, 324/58.5 R

[56] References Cited

FOREIGN PATENT DOCUMENTS

| | | | |
|---|---|---|---|
| 2712600 | 9/1977 | Fed. Rep. of Germany | 324/58.5 A |
| 1560591 | 2/1980 | United Kingdom | 324/58.5 A |
| 1564194 | 4/1980 | United Kingdom | 324/58.5 A |
| 211856 | 4/1968 | U.S.S.R. | 324/58.5 B |
| 217002 | 7/1968 | U.S.S.R. | 324/58.5 A |
| 245439 | 10/1969 | U.S.S.R. | 324/58.5 A |
| 244438 | 10/1969 | U.S.S.R. | 324/58.5 A |

Primary Examiner—Ernest F. Karlsen
Assistant Examiner—Jose M. Solis
Attorney, Agent, or Firm—McAulay, Fields, Fisher, Goldstein & Nissen

[57] ABSTRACT

A method and apparatus for detecting grain direction in wood particularly in lumber by means of high frequency radio energy like microwave radiation. The grain direction in lumber can be detected so that knots will cause no significant error to the measuring result. The knots are detected by the method according to the invention in so far as they contain deviations of grain direction. The microwave radiation is either passed through or reflected from the piece of lumber. Radiation energy is transmitted with the aid of a transmitting antenna with a certain direction of polarization and a signal of grain direction is obtained by detecting microwave field by a receiving antenna whose direction of polarization plane forms an angle of 90° with the direction of polarization plane of transmitting antenna.

A preferred embodiment of the invention provides for the polarization of transmitting field to be changed so that it alternatively is parallel or perpendicular to the direction of polarization plane of receiving antenna. A first signal ($V_s$) is measured when both polarization planes are perpendicular to each other and a second reference signal ($V_{ref}$) is measured when the polarization planes are parallel. The angle of the grain direction is obtained from the result of dividing the first signal with the sum of the first and second signals.

15 Claims, 5 Drawing Figures

METHOD AND APPARATUS FOR DETECTING GRAIN DIRECTION IN WOOD, PARTICULARLY IN LUMBER

CROSS-REFERENCES TO RELATED APPLICATIONS

This application is a continuation-in-part of my earlier U.S patent application Ser. No. 042,517 filed May 25, 1979 and entitled: An Apparatus for Detecting Deviant Grain Direction in Timber, etc. now, abandoned.

FIELD OF THE INVENTION

This invention relates to method and apparatus for detecting grain direction in wood, particularly in lumber.

Deviant grain direction is what the present invention detects. It is the purpose of the present invention to provide a method and an apparatus for detecting deviant grain directions without at the same time being subject to detecting knots or disturbances in the wood caused by knots.

More particularly, the invention relates to the detection of grain direction in wood, particularly in lumber, by means of high frequency radio energy, preferably microwave radiation. The high frequency radio energy is passed through or reflected from a piece of wood to be measured, so that the radiation energy is transmitted by means of a transmitting antenna with a certain direction of polarization, and a signal of grain direction is obtained by detecting the microwave field received by a receiving antenna with a certain direction of polarization.

Grain direction is of great importance to the strength of wood, particularly in lumber. Detection of deviations in the grain direction with respect to the axis of a piece of lumber is of utmost importance in stress grading.

In most industrialized countries, use of only stress-graded lumber in the primary structures of wooden buildings is permissable. The stress grading can be carried out either mechanically or visually.

The currently employed stress grading machines are based on measuring the modulus of elasticity of the lumber. Normally this takes place by bending the lumber. It has been experimentally proven that the modulus of elasticity of lumber is correlated with its strength.

Visual grading is based on an estimation of the basic strength of the lumber and of the defects in the lumber which causes a deterioration of the strength of the lumber. The basic strength is defined according to the density of wood material. The most important types of defects which cause a deterioration of the strength of the lumber are knottiness and slope of grain.

The influence of the knots upon the strength is dependent on the frequency and type of knots in the lumber. In comparison with the surrounding wood material, the knots represent inhomogenous spots and thus weaken the generally homogenous wood material.

Another important factor is grain direction, and the present invention is directed to the detection of this feature. The importance of such detection will be explained. Grain of homogenous wood, and properties such as the tensile strength, compression strength and bending strength of wood are also dependent on grain directions.

Slope of grain, i.e. deviation of grain direction, relates fiber or grain direction to the longitudinal axis of a wood piece. It is the angle between the fibres and the longitudinal axis of the piece of wood.

The advantage of visual estimation is the fact that the observation and localization of the defects is easy. The drawbacks are the randomness and slowness of the estimation, as well as the difficulty in assessing the combined effects of the defects.

DESCRIPTION OF THE PRIOR ART

It is important to consider knots and the detection thereof with respect to the detection of deviant grain directions.

For the purposes of explanation and distinction, it should be noted that the factors influencing the strength of wood, particularly lumber, can also be defined by employing non-contacting measuring methods. The density of wood can conventionally be measured by means of radioactive radiation, according to the mass absorption law. Knots can be observed by using microwave radiation, as is described for example in the British Patent Specification No. 1,489,554 entitled "A method for classifying timber", applicant Innotec Ltd. The slope of grain in wood can be measured capacitively or by employing microwave radiation.

In U.S. Pat. No. 3,805,156 to Norton et al., entitled "Wood slope of grain indicator" there is presented a capacitive method for measuring slope of grain, which method is based on the fact that the dielectric properties of wood are a function of the direction of the grain. This fact makes it possible for an indicator according to the patent to derive a signal from the change in capacitance of a rotating pair of capacitor plates located near the surface of the wood. The slope of grain is determined by comparing the signal's phase with that of a reference signal.

A drawback of the capacitive slope of grain indicator is that the indicator includes both mechanical and electromechanical parts, which are easily worn out and damaged. Moreover, the capacitive sensing element has to be located very near to the piece of wood which is to be measured and at a standard distance therefrom. Consequently, a measuring device of this type is not suitable for continuous, automatic measuring of the slope of grain in moving lumber, because it is difficult if not impossible to maintain the aforesaid standard distance.

There is also disclosed in the Finnish Patent Publication No. 53,365 by the same applicant an invention and disclosure entitled "Apparatus for employing radio frequency energy reflected from or transmitted through timber in order to detect slope of grain"; this is an invention for measuring slope of grain in lumber by using radio frequency energy. In the aforesaid Finnish Patent Publication No. 53,365 high frequency radio energy received from one or more transmitting antennae is allowed to pass through or to reflect from lumber; the radiation received in one or more receiving antennae is then measured, and changes occurring in the amount and/or phase of radiation which has passed through the lumber or which has been reflected from it are interpreted as changes in the quality of the lumber to be measured. This interpretation is based on the fact that wood is an anisotropic material judging by its dielectric characteristics.

In the publication referred to, the system of antennae is constructed by three antennae, two of which form a pair. The antennae forming a pair are interchangeable and can function as either receiving antennae or transmitting antennae. This pair of antennae is positioned in a mutually symmetrical oblique position in relation to the third antenna of the set and to the main direction or the direction of the edges of the lumber. Between the two antennae forming a pair and their common port, a phase difference of 180° is arranged.

Although the arrangement suggested in the Finnish Patent Publication mentioned above makes it possible to detect deviations in the grain direction in lumber, it also involves certain disadvantages. Besides deviant grain direction, the apparatus also provides a strong indication of knots, even if the latter should include no significant deviations of grain direction in the surrounding wood. This makes it extremely difficult to detect the actual amount of slope of grain in lumber with a great deal of knots. The knots effectively mask the grain slope.

U.S. Pat. No. 3,549,986, to Prine is concerned with a microwave system for detecting flaws or the like in a sample. The system is explained in more detail using as an example the situation where the sample under inspection is a vehicle tire. The system employs a detection means which is insensitive to energy transmitted directly from a transmitting antenna and energy reflected from surfaces of the sample, whereas the detection means is highly sensitive to energy scattered by flaws within the sample. In more general terms, the U.S. Pat. No. 3,549,986 presents a system for detecting scattered radio frequency energy caused by inhomogeneities within a sample.

Prine is primarily intended for the detection of inhomogeneities which are further defined throughout as air bubbles, metallic inclusions and flaws. There is no teaching of detecting deviant grain direction.

U.S. Pat. No. 4,123,702 to Kinanen et al, is concerned with a microwave detection system for detecting knots, etc. in timber. The measuring apparatus can be applied for detecting knots under certain reserves. The system also detects the density of timber; in other words, the system detects the variation between parts grown in the summer and in the winter. The measurement does not, however, provide any information concerning grain directions, and the provision of such information in the system would be only harmful, because it would disturb accurate detection of knots.

U.S.S.R. Pat. No. 244,438 to Kovalev et al only teaches checking a product for a foreign body contained therein by using polarized waves. In the USSR-Patent of Kovalev et al., the same kind of arrangement of antennae is disclosed as in the present application.

SUMMARY OF THE INVENTION

The present invention relates to a new method and apparatus for detecting grain direction in wood, particularly in lumber, which method and apparatus is not subject to disturbance caused by knots.

The invention is characterized in that the radiation energy is transmitted by means of one or several transmitting antennae and by employing at least two mutually divergent directions of polarization, whereby the dielectric anisotrophy of wood induces a change in the direction of the polarization and the radiation energy passed through or reflected from wood is received by means of at least one receiving antenna and by employing directions of polarization among which directions at least one is as such characteristically perpendicular to any one direction of polarization of transmitting field.

The main advantage of the invention may be considered to be the fact that it does not provide an indication of knots unless they also involve deviation in grain direction. In addition, an apparatus according to the invention is very simple in its construction.

When determining the slope of grain on the basis of the signal produced by the apparatus described in the Finnish Pat. No. 53,365, this presupposes information concerning the thickness of lumber and its dielectric anisotropy at a particular measurement frequency. Furthermore, it should be noted that dielectric anisotropy also depends on moisture content and density of wood material. These factors cause difficulties for measurement in practice, as the characteristics of lumber show a great deal of variation even in one and the same piece.

The afore-mentioned disadvantage can be avoided with the particular embodiment of the invention in which the measurement of slope of grain is carried out by means of two transmitting fields; the polarizations of these two fields form an angle with each other. In this way, both transmitting field polarizations have their own receiving systems, and the planes of polarization of the receiving systems are at right angles to their respective planes of transmitting field polarizations.

The method according to the invention makes it possible to derive a signal for the grain direction, especially slope of grain, by detecting the microwave power collected by the receiving antenna after passing through or being reflected from the lumber to be measured.

Slope of grain causes elliptical polarization in the transmitted or reflected microwave field, in which case the received field also includes a field component whose polarization is perpendicular to the polarization of the transmitting field. If the polarization of the transmitting field is parallel to the grains in the wood or at a right angle to it, the polarization of the received field is equal to that of the transmitting field. Now, the field component perpendicular to the polarization of the transmitting field is zero.

It has been observed that a signal of $V_s$ characteristic of grain direction is proportional to the product consisting of the following factors: transmitting power P; attenuation factor of wood piece C; and, function f; and these in turn depend on the slope of grain by the angle of grain direction with respect to the transmitting field polarization. The following relationship can be set forth:

$$(1)\ V_s = P \times C \times f \qquad (\alpha);$$

As, on the other hand, the transmitting power and the attenuation factor can be assumed to be constant, i.e.

$$(2)\ K = P \times C = \text{constant};$$

then, the signal of grain direction is in each measurement defined as follows:

$$(3)\ V_s = K \times f \qquad (\alpha).$$

By carrying out two measurements with different polarization of transmitting radiation energy at the same point of lumber, the following equations are obtained:

In measurement 1

$$(4)\ V_{s1} = K \times f \qquad (\alpha_1)$$

In measurement 2

$$(5)\ V_{s2} = K \times f \qquad (\alpha_2)$$

By dividing the equations (4) and (5) with each other, the following equation and relationship is obtained:

$$\frac{V_{s1}}{V_{s2}} = \frac{f(\alpha_1)}{f(\alpha_2)} \qquad (6)$$

Stated differently, it may be confirmed on the basis of equation (6), that the proportion of signals of grain direction is in this case solely dependent on the angle of grain direction with respect to the transmitting field polarization, and not on other possible characteristics of the lumber.

The above described measuring method can be carried out by using either two separate measuring apparatus or, most preferably, by using an apparatus wherein the transmitter can generate waves of different polarizations for transmission by the transmitter and the detection of these different waves in the receiver is carried out by a method which is already a well known microwave technique, and it is therefore unnecessary to further explain it in this context.

According to a preferred embodiment of the invention, it is advantageous to arrange a first measurement in the direction of the polarization of the transmitting field so that it is essentially perpendicular to the length axis of the piece of lumber to be measured. In this case, the polarization of the receiving antenna is then arranged so that it is respectively parallel to the length axis of the lumber.

If the grain direction is parallel to or perpendicular to the polarization of the transmitting field, the received signal will be zero.

It is then advantageous to arrange a second measurement in which the direction of the polarization in the transmitting field is such that it forms an angle of 45° with respect to the lengthwise dimension of the lumber; in this case, the maximum signal will be received from the receiving antenna whose polarization is as in the first measurement if the grain direction is parallel to the lengthwise dimension of the lumber.

According to another embodiment of the invention, the signal of grain direction is normalized in a way which is slightly different from equation (6). It can be theoretically verified that lumber with normal thickness and a normal range of moisture content, that and the angle of grain direction fulfills the following formula of approximation:

$$\frac{V_s}{V_s + V_{ref}} = \sin^2 \alpha, \text{ when } \alpha < 45°.$$

In the formula (7), $V_s$ designates the same signal as in the equation (3).

In this case, it is most preferable to have the polarization direction of the transmitting field parallel to the length axis of the lumber, and the polarization of the receiving field perpendicular to the length axis of the lumber, or vice versa.

$V_{ref}$ designates a signal obtained when both the polarization of the transmitting field and the polarization of the receiving antenna are parallel with each other and both are perpendicular to the length axis of the lumber.

To these ends, the invention is concerned with a system for detecting deviant grain direction in lumber or timber, and includes the transmission of high frequency radio energy in the microwave range in a first polarization direction, the receiving of high frequency radio energy in the microwave range in a second polarization direction, and means for relating a piece of timber whose grain direction is checked and which timber may be placed adjacent to a transmitting means and a receiving means such that the polarized energy transmitted by the transmitting means is received by the receiving means after impinging onto the aforesaid piece of timber whereby the anisotropy of the timber controls and induces a change in the direction of polarization and any variation thereof from the first direction of polarization of the microwave energy received by the receiving means.

The transmitting means includes at least one polarized energy transmitter positioned on one side of the timber for transmitting the microwave energy in the first polarized direction towards the one side of the timber, and the receiving means includes at least one receiver positioned on the same side of the at least one transmitter, the at least one receiver receiving the microwave energy reflected by the timber after the microwave energy transmitted in the first polarized direction is shifted transversely by the deviant grain direction of the timber.

The transmitting means alternatively includes at least one polarized energy transmitter positioned on one side of the timber for transmitting the polarized energy therethrough, and the receiving means includes at least one polarized energy receiver positioned on the other side of the timber, and the receiving means receives the polarized energy transmitted through the timber and shifted transversely by the anisotropic or deviant grain direction of the timber.

The transmitting means can also include at least one transmitting antennae for transmitting the microwave energy in a direction of polarization parallel or perpendicular to the longitudinal axis of the timber.

The transmitting means may also include means for transmitting the microwave energy in a first direction of polarization, parallel to the longitudinal axis of the timber and means for transmitting energy in a second direction of polarization perpendicular to the longitudinal axis of the timber, and the receiving means includes means for receiving energy in a direction of polarization parallel to the longitudinal axis of the timber.

In a specific embodiment, the transmitting means includes at least one transmitting antenna for transmitting the microwave energy in a direction of polarization parallel to the longitudinal axis of the timber and at least another transmitting antenna for transmitting the microwave energy with a direction of polarization transverse to the longitudinal axis of the timber, and the receiving means includes at least one receiving antenna for receiving the polarized energy in the second direction which is transverse to the longitudinal axis of the timber, whereby to derive a first signal characteristic of the deviant grain direction responsive to the energy transmitted by the one transmitting antenna and received by the receiving antenna and to derive a comparative signal in response to the energy transmitted by the other transmitting antenna and received by the receiving antenna based on the transmitted energy and the received energy when the polarization directions thereof are parallel to each other.

The transmitting means includes two transmitting antennae whose planes of polarization form an angle with each other, and the receiving means includes means for receiving energy from each of the two planes of polarization.

The transmitting means may also include at least one polarized energy transmitter positioned on one side of the timber for transmitting the microwave energy in the first polarized direction towards the one side of the timber, and the receiving means includes at least one receiver positioned on the same side of said at least one transmitter, said at least one receiver receiving the microwave energy reflected by the timber after the microwave energy transmitted in the first polarized direction is shifted transversely by the deviant grain direction of the timber.

The invention is also concerned with a method for detecting grain direction in wood, particularly in lumber or timber, by means of high frequency microwave radiation energy which is either passed through or reflected from the piece of wood to be measured and includes transmitting radiation energy by means of one or more transmitting antennae and by employing at least two mutually divergent directions of polarization, the radiation energy being transmitted with the aid by the transmitting antenna with a certain direction of polarization, the dielectric anisotropy of the wood through which the radiation energy is transmitted induces a change in the direction of the polarization, and then receiving the radiation energy passed through or reflected from the wood by means of at least one receving antennae and by employing directions of polarization among which directions at least one is as such characteristically perpendicular to any one direction of the polarization of the transmitting field, and obtaining a signal of grain direction by detecting the microwave field with the receiving antenna with a certain direction of polarization.

At least one of the directions of the polarization of the transmitting field is essentially parallel to the length axis of the lumber to be measured.

The direction of the polarization of the transmitting field is in turn directed as perpendicular to the length axis of the lumber to be measured so that it forms an angle of 45° with respect to the length axis of the lumber and the corresponding signals are received by means of the receiving antenna, the direction of polarization thereof being in each case perpendicular to the polarization of the transmitting field, and thereafter calculating the proportion of the signals which proportion represents a function of the angle of grain direction.

Alternatively, the direction of the polarization of the transmitting field is in turn directed first as parallel to the length axis of the lumber to be measured and second as perpendicular to the length axis of the lumber and a corresponding first signal ($V_s$) and a second signal ($V_{ref}$) are received by the receiving antenna, the direction of the polarization thereof being perpendicular to the length axis of the lumber whereby the grain direction signal is detected by dividing the first signal with the sum of the first and second signals.

Apparatus for carrying out the aforesaid method includes at least one transmitting antenna and one receiving antenna for transmitting and receiving microwave energy either on the same side or the opposite sides of the piece of lumber to be measured, an oscillator for generating the microwave power, a detector for detecting the microwave signal, polarizers for the receiving transmitting antennae, switches by means of which the direction of the polarization of said antennae are chosen, a driver for the switches, and a processing and control unit with a memory for controlling the driver and for calculating the angle of grain direction.

BRIEF DESCRIPTION OF THE DRAWING

Objects, advantages and the nature of the invention will become readily apparent from the detailed description of the invention made in connection with the accompanying drawings, in which:

FIG. 5 illustrates this arrangement also.

DESCRIPTION OF THE PREFERRED EMBODIMENTS

Figure 1:
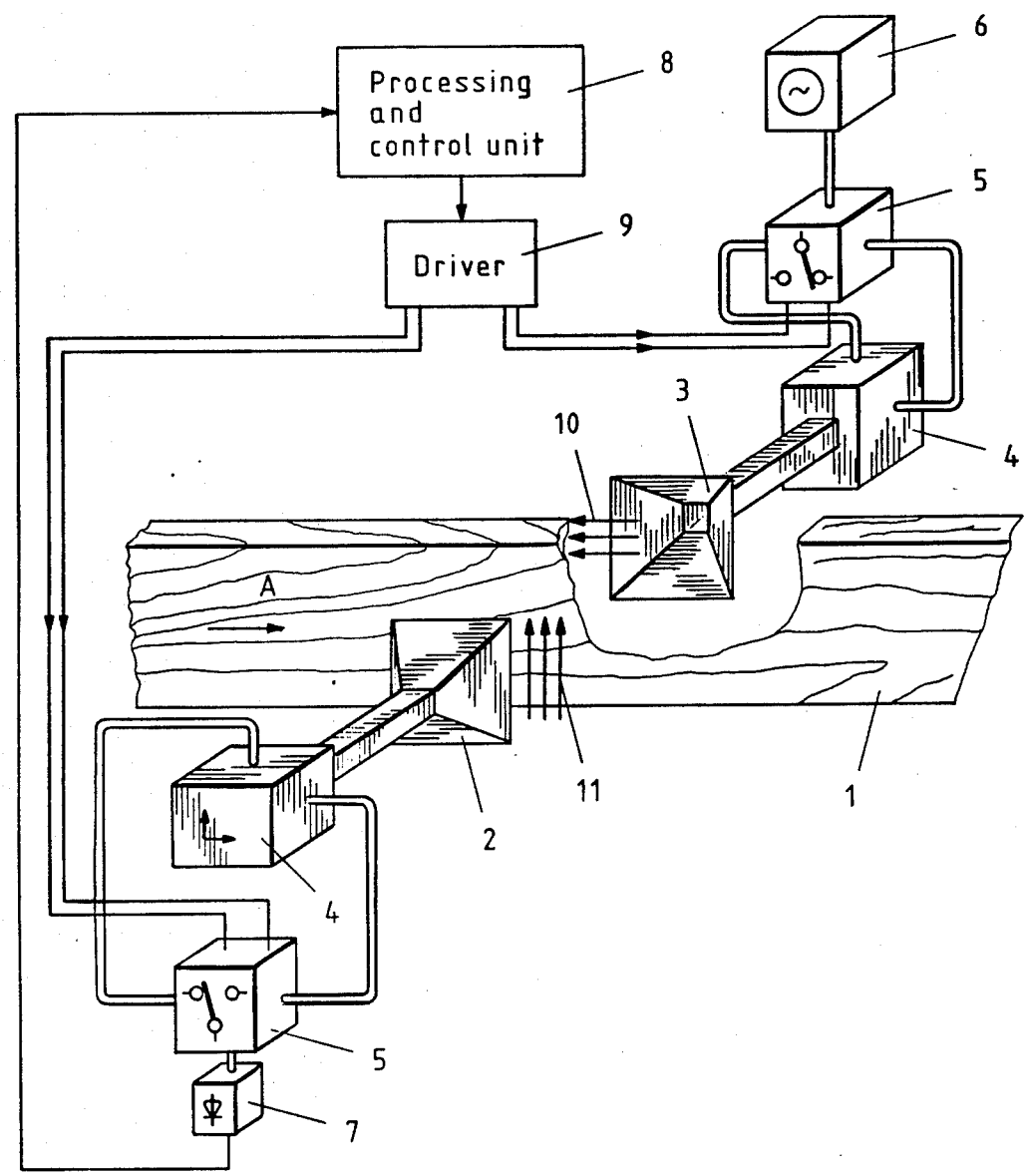
FIG. 1 is a schematic representation of an apparatus according to the invention and particularly useful in connection with the carrying-out of the method.

Referring now to the accompanying drawings which illustrate the best mode for carrying out the invention, and considering in particular FIG. 1 that shows a piece of lumber 1 which is transported in a longitudinal direction as indicated by arrow A by means of a conventional conveyor (not shown); the conveyor is not presented in the drawing because it forms no part of and is not included within the scope of the invention.

The electronic system includes a receiving antennae 2 and a transmitting antenna 3. On one side of the piece of lumber 1, there is located the transmitting antenna 3, which transmits microwave energy. On the other side of the piece of lumber is respectively located the receiving antenna 2, which is employed for receiving the radiation energy which has passed through the piece of lumber 1.

Polarizers 4 are provided for each of the antennas. These polarizers enable the antennas to generate polarized waves having planes of polarization either parallel or perpendicular to the longitudinal axis of the piece of lumber 1, generally indicated by the letter A which also indicates the direction of movement of the lumber.

The polarization of the polarizers 4 can be chosen by means of the SPDT (Single-Pole-Double-Throw) switches 5, for example PIN diode switches. The microwave power is generated in by an oscillator 6. On the receiving side, the microwave signal is detected with a square-law detector 7. The detected measuring signals are fed into a processing and control unit 8, by means of which unit the angle of grain direction is calculated. The processing and control unit 8 also controls a driver 9 for the diode switches 5.

The measuring procedure with the described arrangement takes place preferably in the following manner. Two measurements are carried out. In the first measurement, the polarization of the transmitting field transmitted by antenna 3, whose polarization is illustrated by the electric field vectors 10 in FIG. 1, as parallel to the longitudinal direction of the piece of lumber as indicated by arrow A. The direction of polarization of the receiving antenna is illustrated by the electric field vectors 11, and is in its turn perpendicular to the longitudinal direction of the piece of lumber as indicated by letter A. Thus, the detector voltage is the signal of grain direction $V_s$, which is stored in the memory of the processing and control unit 8.

In a second measurement, the polarization of the electric field perpendicular to the longitudinal direction of the piece of lumber, as indicated by letter A is now employed both in the transmitting and the receiving field by the transmitting antenna 3 and receiving antenna 2, respectively. Now, the detector voltage is $V_{ref}$. By means of the processing and control unit 8, the size of the angle is now calculated in accordance with the formula (7), to provide the angle representing the slope of grain in the piece of lumber.

Figure 2:
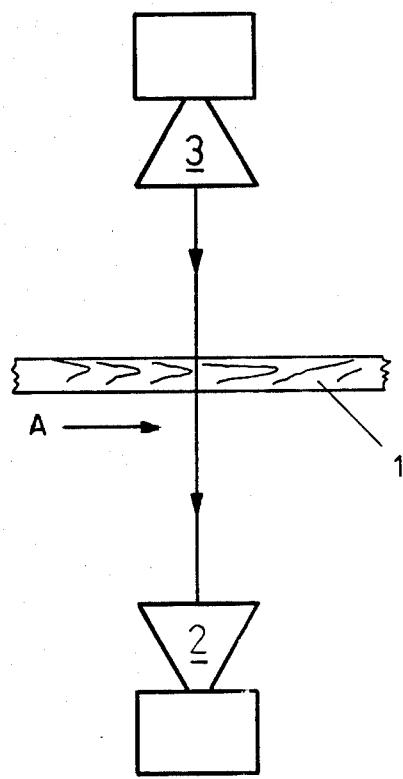
FIG. 2 is a schematic representation of one way to position the transmitting antennae and the receiving antennae, with the transmitting antennae positioned on one side of the piece of lumber and the receiving antennae on the opposite side.
Figure 3:
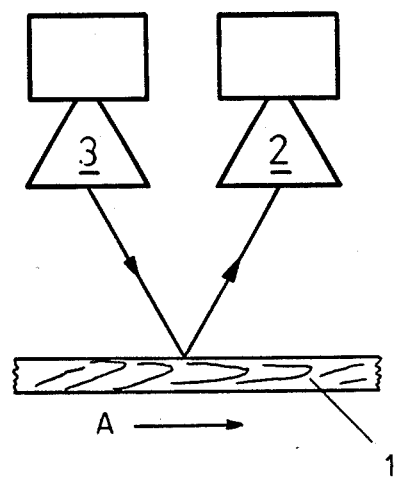
FIG. 3 is a schematic representation of what is a modification of the schematic positioning shown in FIG. 2, with the transmitting and receiving antennas both positioned on the same side of the lumber.

FIGS. 2 and 3 illustrate two different possible antenna arrangements with the same electric field orientation as in FIG. 1. FIG. 2 is a schematic representation of FIG. 1, in which radiation penetrates through the. In FIG. 3 the measuring of the grain direction from the lumber is performed by utilizing the reflected field, as distinguished from measuring the transmitted field as noted in FIGS. 1 and 2.

Figure 4:
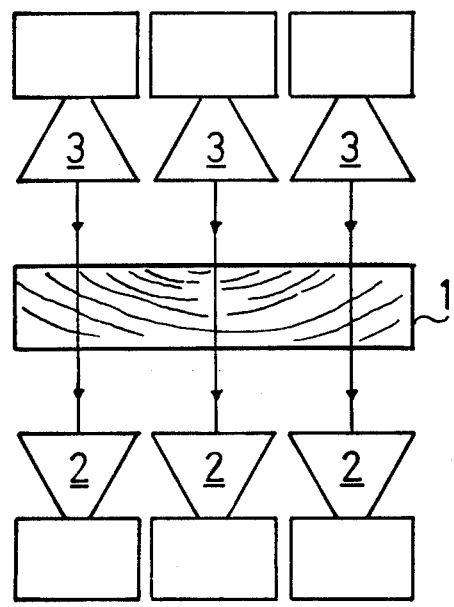
FIG. 4 is another embodiment of the invention in which three transmitting antennas are placed on one side of the lumber, and three receiving antennas are placed on the other side of the lumber.

FIG. 4 illustrates further two possible antenna arrangements based on FIG. 2. In FIG. 4 there are three transmitting antennae 3 and three receiving antennae 2 adjacent to each other respectively in a direction transverse to the direction of the movement of the lumber. The lumber moves in a direction perpendicular to the plane of the paper.

Figure 5:
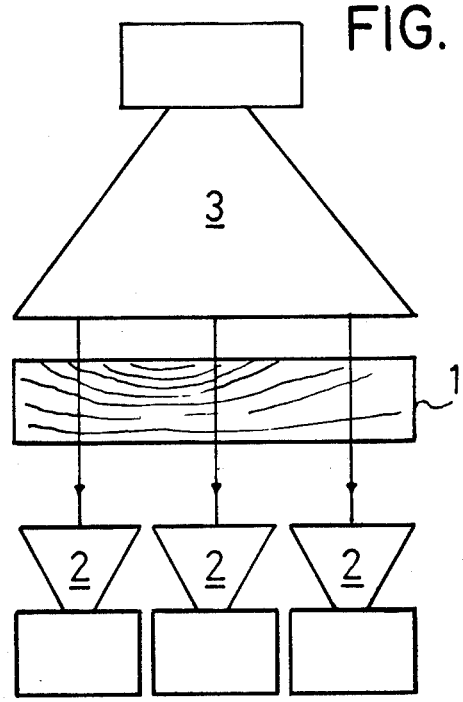
FIG. 5 is another embodiment of the inventions in which a simple transmitting antenna is placed on one side of the lumber, and three receiving antennas are placed on the other side of the lumber. It is also possible to have three transmitting antennas on one side of the lumber and a single receiving antennae on the other side of the lumber.

In FIG. 5, there is only one transmitting antenna 3 and three receiving antennae 2 or this can be also viceversa.

While specific drawings have not been made because the present figures are considered within the scope of an ordinary individual skilled in the act, it should be understood that various charges and modifications can be made to carry out the present invention.

Specifically, while FIG. 5 shows one transmitting antennae 3, and three receiving antennae 2, both the transmitting and receiving antennae can be located on the same side of the piece of lumber and transverse to the longitudinal direction of movement. Movement of the lumber is in a direction perpendicular to the plane of the paper of the drawing. Also, it is within the scope of the teachings of this invention that it is possible to have a single receiving antennae 2 and three transmitting antennae 3. The functions of the antennas in FIG. 5 may be interchanged.

It is clear, based on the aforesaid, that when measuring slope of grain in a broad piece of lumber, there can be one or several adjacent transmitting and/or receiving antennae located on the plane perpendicular to the linear direction A of the piece of lumber, so that the antennae will cover the whole piece of lumber in the transverse direction, and that the measuring can be carried out throughout the width of the piece of lumber.

In the above, the invention has been explained mainly with reference to only one preferred embodiment. The invention is naturally not to be limited exclusively to the described embodiment, but many variations and modifications may be made thereto and these are of course possible without deviating from the central inventive idea presented in the patent claims. Accordingly, in the above description only the term "lumber" has been used, although the invention can naturally be applied to the examination of surfaced sawn lumber or lumber processed in any other way, or even not processed at all.

There is in particular reason to point out that the invention also comprises and includes within its scope, the examination of spiral grain in logs. This can be profitably and preferably carried out by the method of reflection measurement. Now, the arrangements of the antennae must be made according to the demand set by this particular method of measurement, which can be done by any worker skilled in the art as normal construction work, without any special need for inventive activity.

I claim:

1. A method for detecting grain direction in wood, particularly in lumber, by means of high frequency microwave radiation energy which is impinged onto the piece of wood to be measured, comprising the steps of:
    transmitting radiation energy by means of at least one transmitting antenna and by employing two mutually orthogonal directions of polarization;
    transmitting said radiation energy by said transmitting antenna with two mutually orthogonal directions of polarization whereby the dielectric anisotropy of the wood through which the radiation energy is transmitted induces a change in the direction of the polarization; and
    receiving the radiation energy impinged onto the wood by means of at least one receiving antenna and by employing two mutually orthogonal directions of polarization among which directions at least one is as such characteristically perpendicular to any one direction of the polarization of the transmitting field;
    obtaining two signals by detecting the microwave power collected by the receiving antenna with each polarization direction after impinging on said wood; and
    calculating a measure of grain direction from said two signals.

2. A method according to claim 1, wherein at least one of the directions of the polarization of the transmitting field is essentially parallel to the length axis of the lumber to be measured.

3. A method according to claim 1, wherein the direction of the polarization of the transmitting field is in turn directed as perpendicular to the length axis of the lumber to be measured so that it forms an angle of 45° with respect to the length axis of the lumber and the corresponding signals are received by means of the receiving antenna, the direction of polarization thereof being in each case perpendicular to the polarization of the transmitting field, thereafter calculating the proportion of the signals which proportion represents a function of the angle of grain direction.

4. A method according to claim 1, wherein the direction of the polarization of the transmitting field is in turn directed first as parallel to the length axis of the lumber to be measured and second as perpendicular to the length axis of the lumber and a corresponding first signal ($V_s$) and a second signal ($V_{ref}$) are received by the receiving antenna, the direction of polarization thereof being perpendicular to the length axis of the lumber whereby the measure of grain direction is obtained by dividing the first signal with the sum of the first and second signals.

5. An apparatus for detecting grain direction in wood wherein the apparatus includes:
   at least one transmitting antenna and one receiving antenna for transmitting and receiving microwave energy impinged onto the piece of lumber to be measured;
   an oscillator for generating the microwave power;
   a detector for detecting the microwave signal;
   polarizers for said receiving and transmitting antenna for polarizing said transmitting antenna and said receiving antenna initially orthogonally relative to each other;
   switches by which the direction of the polarization of said antenna are chosen and switched;
   a driver for said switches; and
   a processing and control unit with memory for controlling said driver and for calculating the angle of grain direction.

6. A system for detecting deviant grain direction in timber, comprising:
   means for transmitting high frequency radio energy in the microwave range in a first polarization direction;
   means for receiving high frequency radio energy in the microwave range in a second polarization direction orthogonal to said first polarization direction; and
   switch means assocated with said transmitting means for switching said transmitting means to transmit the high frequency energy in a second direction orthogonal to said first direction, said switch means being associated with said receiving means for switching said receiving antenna to receive the high frequency energy in a direction orthogonal to said second polarization direction; and
   means for relating a piece of timber whose grain direction is to be checked and which timber may be placed adjacent to said transmitting means and said receiving means such that the polarized energy transmitted by said transmitting means is received by said receiving means after impinging onto the aforesaid piece of timber whereby the anisotropy of the timber controls and induces a change in the direction of polarization and any variation thereof from the first direction of polarization of the microwave energy received by said receiving means.

7. The system of claim 6, in which
   said transmitting means includes at least one polarized energy transmitter positioned on one side of the timber for transmitting the microwave energy in the first polarized direction towards the one side of the timber; and
   said receiving means includes at least one receiver positioned on the same side of said at least one transmitter,
   said at least one receiver receiving the microwave energy reflected by the timber after the microwave energy transmitted in the first polarized direction is shifted transversely by the deviant grain direction of the timber.

8. The system of claim 6, in which
   said transmitting means includes at least one polarized energy transmitter positioned on one side of the timber for transmitting the polarized energy therethrough;
   said receiving means includes at least one polarized energy receiver positioned on the other side of the timber; and
   said receiving means receiving the polarized energy transmitted through the timber and shifted transversely by the anisotropic or deviant grain direction of the timber.

9. The system of claim 7 or 8, in which
   said transmitting means includes at least one transmitting antennae for transmitting the microwave energy in a direction of polarization parallel to the longitudinal axis of the timber.

10. The system of claim 7 or 8, in which
    said transmitting means includes at least one transmitting antennae for transmitting the microwave energy in a direction of polarization perpendicular to the longitudinal axis of the timber.

11. The system of claim 6 in which
    said transmitting means includes first means for transmitting the microwave energy in a first direction of polarization, parallel to the longitudinal axis of the timber and second means for transmitting energy in a second direction of polarization perpendicular to the longitudinal axis of the timber; and
    said receiving means includes means for receiving energy in a direction of polarization parallel to the longitudinal axis of the timber.

12. The system of claim 6, in which
    said transmitting means includes at least one transmitting antenna for transmitting the microwave energy in a direction of polarization parallel to the longitudinal axis of the timber and at least another transmitting antenna for transmitting the microwave energy with a direction of polarization transverse to the longitudinal axis of the timber, and
    said receiving means includes at least one receiving antenna for receiving the polarized energy in the second direction which is transverse to the longitudinal axis of the timber, whereby to derive a first signal characteristic of the deviant grain direction responsive to the energy transmitted by said one transmitting antenna and received by said receiving antenna and to derive a comparative signal in response to the energy transmitted by said other transmitting antenna and received by said receiving antenna based on the transmitted energy and the received energy when the polarization directions thereof are parallel to each other.

13. The system of claim 6, wherein said transmitting means includes two transmitting antennae whose planes of polarization form an angle with each other, and the receiving means includes means for receiving energy from each of the two planes of polarization.

14. The system of claim 6, in which
    said transmitting means includes at least one polarized energy transmitter positioned on one side of the timber for transmitting the microwave energy in the first polarized direction towards the one side of the timber, and
    said receiving means includes at least one receiver positioned on the same side of said at least one transmitter, said at least one receiver receiving the microwave energy reflected by the timber after the microwave energy transmitted in the first polarized direction is shifted transversely by the deviant grain direction of the timber.

15. The method of claim 1, wherein said radiation energy is transmitted along certain directions of polarization, at least one of said directions being essentially parallel to the lengthwise axis of said wood.

* * * * *